United States Patent
Tsai et al.

(10) Patent No.: US 6,784,313 B2
(45) Date of Patent: Aug. 31, 2004

(54) PROCESS FOR PRODUCING CARBOXYLIC ACIDS

(75) Inventors: Chia Jung Tsai, Kaohsiung (TW); Yao Lung Liu, Kaohsiung (TW); Hsi Chin Tsai, Chia-Yi (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 10/263,643

(22) Filed: Oct. 4, 2002

(65) Prior Publication Data

US 2003/0130540 A1 Jul. 10, 2003

(30) Foreign Application Priority Data

Oct. 5, 2001 (TW) ........................................ 90124658 A

(51) Int. Cl.⁷ .................. C07C 51/10; C07C 51/12; C07C 51/14
(52) U.S. Cl. .................. 562/406; 562/517; 562/519
(58) Field of Search ................ 562/406, 517, 562/519

(56) References Cited

U.S. PATENT DOCUMENTS

| | | | |
|---|---|---|---|
| 4,212,989 A | * 7/1980 | Isshiki et al. | ................ 560/232 |
| 4,336,399 A | 6/1982 | Isshiki et al. | .................. 560/61 |
| 4,433,165 A | 2/1984 | Singleton | ..................... 562/519 |
| 4,670,570 A | 6/1987 | Wegman et al. | ............... 556/18 |
| 4,733,006 A | 3/1988 | Singleton et al. | ............ 562/519 |
| 5,144,068 A | 9/1992 | Smith et al. | .................. 562/519 |
| 5,281,751 A | * 1/1994 | Schreck | ........................ 562/519 |
| 5,442,107 A | 8/1995 | Beevor et al. | ................ 562/519 |
| 5,488,153 A | 1/1996 | Baker et al. | .................. 562/519 |

FOREIGN PATENT DOCUMENTS

| | | |
|---|---|---|
| EP | 0055618 A1 | 12/1981 |
| EP | 0153834 A1 | 2/1985 |
| GB | 1538783 | 1/1979 |

OTHER PUBLICATIONS

Werner Bertleff, "5. Carbonylation of Alcohols and Ethers," taken from Ullmann's Encyclopedia of Industrial Chemistry, Wiley–VCH Verlag GmbH & Co., (Jun. 15, 2000).*

Nagy–Magos et al, "Amino Acid Dicarbonylrhodium (l) Complexes" Transition Metal Chemistry, vol. 5 pp. 186–188 (1980).*

Hirai et al, "Direct Conversion of Allylic Alcohols into N–acyl–alpha–Amino Acids by Catalytic Amidocarbonylation by Means of Homogenous Binary Systems" Tetrahedron Letters, vol. 23(24), pp. 2491–2494 (1982).*

* cited by examiner

*Primary Examiner*—Deepak Rao
*Assistant Examiner*—Zachary C. Tucker
(74) *Attorney, Agent, or Firm*—Birch, Stewart, Kolasch & Birch, LLP

(57) ABSTRACT

A process for producing a carboxylic acid having (n+1) carbon atoms, which includes carbonylating an alcohol having n carbon atoms, and/or an ester of the alcohol and the carboxylic acid in each alkyl group with carbon monoxide in the presence of a catalytic system containing a rhodium catalyst. The process uses a reaction medium for the carbonylation that includes: (1) a rhodium catalyst, (2) an organic halide corresponding to said alcohol, (3) an ester of the alcohol and the carboxylic acid, (4) the carboxylic acid, optionally (5) water, a haloid acid, an inorganic halogen salt or an acetate, and (6) a cocatalyst selected from arginine, N-acetyl alanine, or nitrogen- and oxygen-containing organic compounds.

20 Claims, No Drawings

PROCESS FOR PRODUCING CARBOXYLIC ACIDS

This nonprovisional application claims priority under 35 U.S.C. §119(a) on Patent Application No. 90124658 filed in TAIWAN on Oct. 5, 2001, which is herein incorporated by reference.

BACKGROUND OF THE INVENTION

1. Field of the Invention

The present invention relates to a process for producing carboxylic acids, and more particularly to a process for producing acetic acids by the carbonylation of methanol with carbon monoxide. The process is characterized by introducing one or more specific organic compounds containing nitrogen and oxygen in the presence of a catalytic system containing rhodium catalyst. The organic compounds are used as cocatalyst for the catalytic system so as to increase rhodium concentration contained in a reaction medium, thereby carrying out the reaction within wider operation limits and under relatively severe conditions.

2. Description of the Related Art

The preparation of acetic acids by rhodium-catalyzed carbonylation of methanol and carbon monoxide is a well known process, which has been operated upon a commercialized scale for several decades. The process comprises carbonylizing an alcohol having n carbon atoms with carbon monoxide into a carboxylic acid having (n+1) carbon atoms in liquid phase in the presence of a dissolved homogeneous rhodium catalyst and a promoter such as an organic iodide compound.

In such process, carbonylation is usually carried out at an elevated temperature (for example 185~190° C.) and at a high pressure (for example 20~35 $kg/cm^2$). Since the rhodium catalyst is present in a form of rhodium (I), such unstable rhodium (I) catalyst is readily oxidized into an inactive form of rhodium (III) to be precipitated off under the above condition. Therefore, it is necessary to add appropriate amount of water and hydroiodic acid for enhancing rate of carbonylation and maintaining stability of the catalyst system. For example, it is suggested by Monsanto Company (one of the earliest companies to develop such production process of acetic acid) that this process is operated by using 14% of water and 1.17 mole/l of iodide.

It has been found that precipitation of insoluble rhodium (III) species has the tendency to occur when partial pressure of carbon monoxide is at a low level and the water used is less than 14% by weight. Since this commercialized process results in some problems, many patents are directed to methods for overcome the precipitation problem in the past several decades.

U.S. Pat. No. 4,733,006 discloses the use of inorganic salt additives XOAc ($X=Li^+$, $Na^+$, $K^+$), however, the effect of the inorganic salt additives on reaction rate is not described.

GB Patent No. 1,538,783 discloses a process for producing acid anhydride by using Group IV B, V B, VI B or VIII B transition metal as a catalyst and organic trivalent nitrogen or phosphorous compound as a catalyst stabilizer. The organic nitrogen compound represents amine compound with a substituent of hydroxy, epoxy, aromatic, nitrile groups, etc. It is said in this patent that such organic compounds are effective to stabilize catalyst and reduce corrosion.

U.S. Pat. No. 4,336,399 mentions trivalent nitrogen-containing organic amine compounds, which are readily to form quaternary ammonium compounds in reaction mediums so as to increase the concentration of free iodine. Thus, the amine compound indirectly makes the catalyst system more stable, but the amine compound itself has no efficacy of directly stabilizing catalysts.

Moreover, some patents allows for using heterocyclic compounds having simply nitrogen as catalyst stabilizers, for example N-methylimidazole described in EP 0 153 834 and bipyridin described in U.S. Pat. No. 4,433,165. Another example is U.S. Pat. No. 5,442,107, wherein the nitrogen-containing heterocyclic compounds selected from the following are use as catalyst stabilizers in carbonylation of methanol at a low water content:
(1) 2-ethyl-4-methyl imidazole,
(2) 4-methyl imidazole,
(3) 4-t-butyl-pyridine,
(4) 2-hydroxy-pyridine,
(5) 3-hydroxy-pyridine, and
(6) 4-hydroxy-pyridine.

The nitrogen-containing heterocyclic compounds mentioned in the above three patents, however, will react with iodide in reaction mediums to form quaternary ammonium iodide salts under severe conditions such as low content of water and high concentration of organic iodine. The quaternary ammonium iodide salts can form insoluble complexes with rhodium and thus the catalyst stabilization is lost. Further, the insoluble complexes may be precipitated from the reaction solution of the carbonylation of methanol at a low water content. In these prior arts, it has not been mentioned or implied that the pyridine derivatives having substituents other than OH group and alkyl group have effects on reducing precipitation of the rhodium catalyst in the carbonylation of methanol at a low water content.

U.S. Pat. No. 5,144,068 teaches the use of inorganic iodide LiI as a catalyst stabilizer in the carbonylation of methanol. This stabilizer improves the precipitation of the rhodium catalyst under the condition of a low water content, and an approximately identical reaction rate to that of the reaction system at high water content (e.g. 14% by weight) is achieved. According to this patent, a quaternary ammonium salt, i.e. N-methyl-picolinium iodide, is employed at a low water content to increase the reaction rate of carbonylation. However, it is found that N-methyl-picolinium iodide readily reacts with rhodium to forms an insoluble complex, which may be precipitated from the reaction solution.

U.S. Pat. Nos. 4,670,570 and 5,488,153 teach the use of phosphorus-containing compounds such as [P~P=S](CO)Cl, [P~P=O](CO)Cl and [P~COCH₃](CO)Cl as a material for stabilizing the rhodium catalyst. However, there still exist the following disadvantages: (1) although phosphorus is a strong ligand, one coordinate bond needs to be dissociated for exposing rhodium (I) species during the reaction, and thus the oxidation addition of methyl iodide can be carried out; in addition, the strength of each coordinate bond of the phosphorus-containing compound is substantially identical, which means that the whole phosphorus-containing compound might be dissociated from rhodium atom in the reaction system so as to result in the precipitation of rhodium. (2) The dissociated free phosphorus may react with trace oxygen and methyl iodide in the system to form phosphorus oxide and phosphorus iodide, respectively, and thus the inherent strong coordinating ability of phosphorus is lost. In addition, it is also disadvantageous to have relatively high activation energy for performing the reaction and add excess amount of triphenylphosphine to keep its activity.

EP 0 055 618 discloses the addition of an organic catalyst stabilizer into the reaction solution for reducing the precipitated amount of the rhodium catalyst in the carbonylation of methanol due to a low water content. The stabilizer employed in this patent is selected form one or more organic compounds containing one or more nitrogen atoms, phosphorus atoms or COOH groups:
(1) N,N,N',N'-tetramethyl-o-phenylene diamine and 2,3'-dipyridyl;
(2) HOOC—$Y_1$—COOH and (HOOC—$Y_2$)(HOOC—$Y_3$)N—$Y_1$—N($Y_4$—COOH) ($Y_5$—COOH), where $Y_{1-5}$=$(CH_2)_m$; and
(3) $(R_1)(R_2)P$—$R_3$—$P(R_4)(R_5)$, where $R_{1-5}$ is alkyl.

Since the type and number of these functional groups are not as good as those used in the present invention, such catalysts have relatively poor stabilizing effect.

Although some organic or inorganic salt additives for reducing or avoiding the precipitation of rhodium under low partial pressure of carbon monoxide and at a low water content are provided in the above-described prior arts, there still exist some drawbacks required to be overcome. Therefore, it is necessary to provide a cocatalyst for efficiently stabilizing a rhodium catalyst under a severe reaction condition of carbonylation so as to reduce the precipitation of rhodium.

SUMMARY OF THE INVENTION

The present invention relates to a process for producing a carboxylic acid. The process comprises carbonylating an alcohol having n carbon atoms, an ester of the alcohol and the carboxylic acid or a dialkyl ether having n carbon atoms in each alkyl group with carbon monoxide in the presence of a catalytic system containing a rhodium catalyst so as to produce the carboxylic acid having (n+1) carbon atoms, the process is characterized by using a reaction medium for the carbonylation comprises: (1) a rhodium catalyst; (2) an organic halide corresponding to the alcohol; (3) an ester of the alcohol and the carboxylic acid; (4) the carboxylic acid; optionally (5) water, a haloid acid, an inorganic halogen salt or an acetate; and (6) a cocatalyst selected from one or more nitrogen- and oxygen-containing organic compounds represented by the following formula:

where $R_1$, $R_2$ and $R_3$ are identical or different, and each represents:

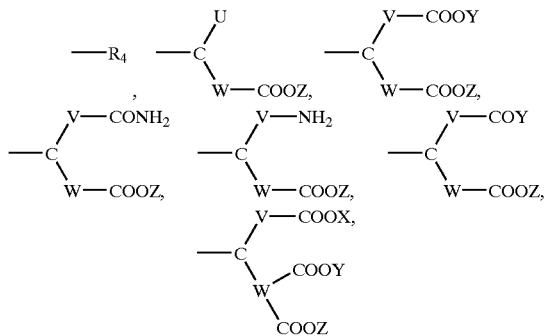

where $R_4$ represents H, an aliphatic group having 1 to 6 carbon atoms, or an arylaliphatic or an aromatic group having 6 to 10 carbon atoms;

U represents H, aliphatic group having 1 to 6 carbon atoms or an arylaliphatic group or aromatic group having from 6 to 10 carbon atoms;

V and W are identical or different, and each represents a covalent bond, an aliphatic group having from 1 to 6 carbon atoms or an arylaliphatic group or aromatic group having 6 to 10 atoms; and X, Y and Z are identical or different, and each represents H, metal ion or an aliphatic group having 1 to 6 carbon atoms, with the proviso that at least one of $R_1$, $R_2$ and $R_3$ is a group other than $R_4$.

DETAILED DESCRIPTION

The term "organic halide corresponding to said alcohol" used herein means those obtained by replacing the hydroxyl group of said alcohol with a halogen atom. For example, when said alcohol is methanol, the organic halide corresponding to said alcohol is methyl halide, such as methyl iodide. The organic halide is used as a promoter of the carbonylation according to the present invention.

The example of "optionally inorganic halogen salt or acetate" used herein includes, for example, halogen salt or acetate of alkali metal, alkaline-earth metal or transition metal.

The cocatalyst of the present invention, which is different from the stabilizers of the rhodium catalyst used in the above prior patents, is an organic compound containing both nitrogen and oxygen. The nitrogen of this organic compound has strong coordinating ability to be bonded to aliphatic groups, aromatic groups or aliphatic-aromatic groups on the nitrogen atom, but the oxygen-containing functional group has relatively weaker coordinating ability. Thus, the coordinate bonds have distinct strength. These cocatalysts can form rhodium catalyst complexes with rhodium compounds such as rhodium chloride, rhodium iodide or rhodium acetate (optionally treated for example by reducing the trivalent rhodium into a monovalent one). Since the number of coordinate bonds of the rhodium catalyst complexes reaches saturation and the structure thereof has the tendency to be stable, the stability of the rhodium catalyst complexes in the liquid reaction medium is largely increased. Furthermore, when oxidation addition of the organic halide promoter, e.g. methyl iodide, is performed on rhodium, the strong coordinating atoms (i.e. the nitrogen atom) of the cocatalyst keeps forming coordinate bonds with rhodium. Meanwhile, the coordinate bonds between the weak coordinating atoms (i.e. the oxygen atom) and rhodium dissociate, and thus the rhodium atoms are exposed to allow rhodium to carry out the catalytic reaction. Subsequently, when the product of carbonylation is separated, the weak coordinating atoms of the cocatalyst quickly form coordinate bonds with rhodium again. Hence, the cocatalyst of the present invention can prevent the rhodium complex from attacking by other halogen atoms in the reaction medium, so as to maintain the stable valence state of rhodium. Comparing with the rhodium complex of rhodium and the stabilizers having identical strength of coordinate bonds and mentioned in the U.S. Pat. Nos. 5,488,153 and 4,670,570, such as [P~P=S](CO)CI, [P~P=)](CO)Cl and [P~COCH3](CO)Cl, the rhodium complex of rhodium and the cocatalyst of the present invention has significantly excellent performance on the composition structure and the stabilization.

In comparison with N-methylimidazole described in EP 0 153 834, bipyridine in U.S. Pat. No. 4,433,165, imidazole and pyridine compounds in U.S. Pat. No. 5,442,107 and the organic nitrogen-containing amines (III), the cocatalyst according to the present invention is distinguished by containing oxygen in addition to nitrogen. Such a cocatalyst is favored to form coordinating bonds of different strength and increase the solubility. Thus, the cocatalyst of the present invention has better stabilizing effect than that disclosed in the prior art.

The examples of cocatalyst suitable to be used in the present invention include carboxylalkyl amines such as tri(carboxylmethyl) amine, di(carboxylmethyl) amine, methyl-di (carboxylmethyl) amine or 3-amino-1, 1,3-propane-tricarboxylic acid; amino acids such as tyrosine, aspartic acid, β-methyl-aspartic acid, glutamic acid, arginine, glutamine or lysine; the derivatives of amino acids such as N-(methoxyl) ethylamino acid or acetyl-alanine; and the metal salts thereof.

The cocatalyst of the present invention has excellent effects on stabilizing rhodium catalysts. For example, the cocatalyst can assist the rhodium metal in the reaction medium to be maintained at the active monovalent state even under severe reaction conditions mentioned in the prior art such as high concentration of organic halogen (e.g. greater than 10 wt %), high concentration of ester (e.g. greater than 1.5 wt %), low partial pressure of carbon monoxide (less than 12 Kg/cm$^2$) and low water content (e.g. less than 14 wt %), thereby minimizing the precipitation of rhodium. Since the conventional rhodium catalysts lack any protective structure, they are readily oxidized to lose their activity and precipitate, and it is required to add excess hydroiodic acid for maintaining their catalytic activity. Unlike the conventional catalytic system, a lesser amount of hydroiodic acid is effective in the reaction medium of the present invention, thereby minimizing the problem of equipment corrosion resulted from the addition of hydroiodic acid.

In addition, if addition of hydroiodic acid is required to maintain a high catalytic activity, the cocatalyst of the present invention can form quaternary ammonium salts with free halogen ions in the reaction medium so as to maintain a stable concentration of free halogen ions. That is to say, the cocatalyst of the present invention can indirectly improve the catalytic efficiency.

Moreover, in the typical system for producing acetic acids by carbonylating methanol with carbon monoxide, it is generally necessary to be in the presence of 14~15 wt % of water in the reaction medium for increasing the solubility of the rhodium catalyst and the catalytic activity thereof. However, in the present invention, since rhodium catalysts and the cocatalyst of the present invention form stable complexes, the catalyst precipitation due to the decrease of water content can be partially or entirely overcome. Generally, the lower the water content in the reaction system is, the more amount of the cocatalyst is required. When the concentration of the cocatalyst increases to a certain level, the concentration of the rhodium catalyst in the liquid reaction medium can maintain the same level as that at higher water content. Therefore, in the presence of the cocatalyst of the present invention, the water content of the reaction system can be reduced. With the cocatalyst of the present invention, the load on the separation equipment will be reduced and the benefit of investment is obvious.

According to the present invention, the suitable and preferred concentration ranges of respective components in the homogeneous reaction medium under stable conditions are shown in Table 1.

TABLE 1

Suitable and preferred concentration of respective component in the reaction medium

| Component of reaction medium | Suitable range | Preferred range |
| --- | --- | --- |
| Rhodium catalyst | 200~5,000 ppm | 500~2,000 ppm |
| Organic halide promoter | 5~40 wt % | 10~30 wt % |
| Ester of alcohol and carboxylic acid | 0.1~30 wt % | 0.1~5 wt % |
| Water | 0~20 wt % | 1~10 wt % |
| Hydroiodic acid, inorganic halogen salts or acetates | 0~30 wt % | 3~20 wt % |
| Mole ratio of cocatalyst/rhodium catalyst | 0.5~200 | 1~100 |

The present invention is particularly suitable for use in a process for producing acetic acids by carbonylating methanol with carbon monoxide, wherein the reaction medium preferably includes the rhodium catalyst (500~2000 ppm), methyl iodide (10~30% by weight), methyl acetate (0.1~5% by weight), water (1~10% by weight), the cocatalyst (has a mole ratio to the rhodium catalyst in a range of 1~100), optional hydroiodic acid, inorganic halogen salts or acetates (3~20%), the product acetic acid and a little impurity.

Industrial Applications of the Invention

Overall, due to the presence of the specific cocatalyst in the reaction medium, the process for producing carboxylic acid according to the present invention has the following advantages of:

1. stabilizing rhodium catalysts and reducing the precipitation of the rhodium catalysts, thereby indirectly increasing the catalytic efficiency;

2. allowing the carbonylation to be carried out under highly catalytic condition: in the typical catalytic system, although the carbonylation rate can be largely increased under the highly catalytic condition of high organic halogen and high esters concentrations, an undesirable side reaction of rhodium precipitation occurs; however, the side reaction of rhodium precipitation by adding the cocatalyst of the present invention into the reaction medium is avoided, thereby carrying out the carbonylation in the high catalytic condition and further increase yield;

3. allowing the carbonylation to be carried out under a low water content condition: since the cocatalyst of the present invention can largely reduce the rhodium precipitation due to low water content, the carbonylation is able to be carried out under the reaction system at low water content; due to the decrease of water content, more acetic acids can be charged into the reactor of the same capacity; the load of the subsequent equipments for separation and purification will be also decreased so as to increase the yield; furthermore, the corrosion problem of the reaction system due to high water content can be avoided so as to increase the investment benefit;

4. reducing the acid corrosion problem of the reaction system: since the concentration of hydroiodic acid in the reaction medium can be properly reduced in the presence of the cocatalyst of the present invention, the dissociation of strong acid due to high concentration of hydroiodic acid can reduce, thereby further reducing the acid corrosion problem of the system and largely reducing the investment cost.

EXAMPLE

The present invention will now be described more specifically with reference, but not limited to the following embodiments.

The major equipment used in the present invention includes a 1-liter reactor made of anti-corrosive material and a tank for storing carbon monoxide. The reactor is equipped with a variable motor capable of controlling rotation speed thereof, thereby maintaining excellent gas-liquid mixing effect by adjusting the rotation speed. The inside and outside of the reactor are respectively provided with a cooling spiral-pipe and an electrical heater for controlling and maintaining the reaction temperature. Furthermore, a pressure-adjustable control valve is provided between the reactor and the tanks of nitrogen and the carbon monoxide for maintaining and controlling the pressure of the reactor.

The examples of the present invention are carried out in reference to experimental procedures for testing catalyst stabilization described in U.S. Pat. No. 5,442,107. A mixture comprising the catalyst, the organic halide promoter, water, the cocatalyst and optionally hydroiodic acid or inorganic halogen salts is directly introduced into the reactant, and then the reaction is carried out at a certain temperature and a certain pressure. The differences between the modified method according to the present invention and the method disclosed in the above patent are that the reactor is maintained at a pressure of 400 psi and a temperature of 185° C., and the reactant and carbon monoxide are kept in a proper ratio during the initial period of the reaction. In such way, little amount of ester exists in the reaction medium after the reaction is finished so that the load of catalyst is maintained and catalyst instability is increased for observing the change of the rhodium catalyst precipitation in a short time.

According to the experimental requirement, a proper amount of reaction solution is sampled from a sampling outlet of the reactor during operation. The samples are analyzed by means of gas chromatography analysis, iodine titration and atomic absorption spectrometry, and the precipitation of rhodium is observed according to the analytic data, thereby determining the performance of the cocatalyst. In the following examples, all analytic data of the rhodium concentration from the analysis of atomic absorption spectrometry is obtained by using a standard analysis method of employing dimethyl-formamide solution to dissolve rhodium, which is described in Monsanto process. The unit for all the analytic data is ppm.

Example 1

In this example, carbonylation is carried out in the absence of the cocatalyst of the present invention. This example is regarded as a comparative example. With well mixing, 16 g of 2% dicarbonyldiiodide rhodium is introduced into a solution containing 301.3 g of acetic acid, 56 g of methyl iodide, 11.65 g of hydroiodic acid, 11.65 g of water and 20 g of methanol. The reaction mixture is then charged into a reactor, and the reactor is pressurized with carbon monoxide to a pressure of 15 kg/cm². After this pressure is reached and the temperature of the reactor is increased to 185° C., the reactor is pressurized to 28.5 kg/cm² with nitrogen. At that time, the composition of the reaction medium is shown in the Table 2.

TABLE 2

| Initial composition of reaction medium | |
|---|---|
| concentration of rhodium catalyst | 800 ppm |
| concentration of methyl iodide | 14 wt % |
| water | 5 wt % |
| methyl acetate | varied with time |
| acetic acid | balance |

With the consumption of carbon monoxide during the reaction, nitrogen is continuously supplied for maintaining the pressure of the reactor at 28.5 kg/cm². After the reaction is started, samples are taken from the reaction medium every 10 minutes. The samples are analyzed by means of gas chromatography analysis, iodine titration and atomic absorption spectrometry, and the precipitation of rhodium is observed. The operation time of the reaction is 60 minutes.

Examples 2~4

In examples 2, 3 and 4, the carbonylation is carried out under the same condition as that in example 1, except that 4,000 ppm of tri(carboxylmethyl)amine, trisodium tri(carboxylmethyl)amine and sodium glutamate are added to the reaction medium as cocatalysts, respectively.

During 60-minute reaction time, the concentration of the rhodium catalyst in the reaction medium changed with the reaction time is reported in Table 3. It is apparent from Table 3 that the cocatalyst of the present invention is indeed capable of stabilizing the rhodium catalyst and reducing the precipitation of the rhodium catalyst at the reaction system with low water content (5% by weight).

TABLE 3

Stabilizing effect of cocatalyst on rhodium catalyst

| Example No. | Type of cocatalyst | Concentration of rhodium catalyst (ppm) | | | | | | |
|---|---|---|---|---|---|---|---|---|
| | | 0 min | 10 min | 20 min | 30 min | 40 min | 50 min | 60 min |
| 1 | — | 616 | 547 | 362 | 249 | 171 | 117 | 74 |
| 2 | tri-(carboxyl-methyl)-amine | 573 | 572 | 555 | 415 | 313 | 214 | 153 |
| 3 | trisodium tri-(carboxyl-methyl) amine | 669 | 668 | 655 | 609 | 513 | 448 | 388 |
| 4 | sodium glutamate | 620 | 618 | 576 | 509 | 422 | 347 | 289 |

\* other reaction conditions: 5 wt % of water, 14 wt % of methyl iodide, 1~3% of methyl acetate at 10 min, 1~2% at 20 min and 0.5–1% after 30 min.
\* initial concentration of rhodium catalyst is 800 ppm, and the concentration is reduced to about 573~669 ppm when the reaction temperature is reached.

Examples 5~9

In examples 5~9, for a purpose of understanding the impact of the concentration of cocatalyst used in the present invention on stabilizing the rhodium catalyst under a severe condition, the concentration of methyl iodide is increased to 20 wt % and further 1500 ppm cobalt ion (cobalt carbonate) is added to maintain the concentration of ion in the solution at about 1 wt %. Furthermore, 0, 2000, 4000, 8000 and 16000 ppm of tri(carboxylmethyl)amine are added in examples 5~9, respectively.

During 60-minute reaction time, the concentration of the rhodium catalyst in the reaction medium changed with the reaction time is reported in Table 4. As shown in Table 4, when the mole ratio of cocatalyst to rhodium catalyst increases from 1 to 8, the stabilizing effect gradually increases and is not affected by the reaction condition such as low water content (5 wt %) and high concentration of methyl iodide (20 wt %)

TABLE 4

Stabilizing effect of tri(carboxylmethyl)amine with various concentrations on rhodium catalyst

| Example No. | Concentration of cocatalyst (ppm) | Concentration of rhodium catalyst (ppm) | | | | | | |
|---|---|---|---|---|---|---|---|---|
| | | 0 min | 10 min | 20 min | 30 min | 40 min | 50 min | 60 min |
| 5 | 0 | 591 | 462 | 161 | 39 | 11 | 9 | 7 |
| 6 | 2000 | 611 | 552 | 375 | 262 | 186 | 131 | 96 |
| 7 | 4000 | 621 | 549 | 477 | 407 | 336 | 273 | 220 |
| 8 | 8000 | 639 | 547 | 523 | 509 | 466 | 430 | 382 |
| 9 | 16000 | 629 | 556 | 564 | 557 | 562 | 574 | 506 |

* other reaction conditions: 5 wt % of water, 20 wt % of methyl iodide, 1~3% of methyl acetate at 10 min, 1~2% at 20 min and 0.5~1% after 30 min.

Examples 10~11

The carbonylation is carried out at the same conditions as those in examples 5~9 except that the water concentration increases to 7 wt %. During 60-minute reaction time, the concentration of the rhodium catalyst in the reaction medium changed with the reaction time is reported in Table 5. The results of examples 7 and 9, which operated at low water content (5 wt %), are also shown in Table 5 for comparison.

It is shown in Table 5 that when the cocatalyst is at a lower concentration such as 4,000 ppm in examples 7 and 10, the concentration of the rhodium catalyst is still affected by water content in the reaction system. That is to say, the concentration of the rhodium catalyst in the reaction system with lower water content (e.g. example 7) is lower than that with higher water content (e.g. example 10). In contrast, when the concentration of the cocatalyst is increases to 16000 ppm (e.g. examples 9 and 11), there is no significant difference between the concentration of the rhodium catalyst in the reaction system with lower water content (e.g example 9) and that with higher water content (e.g. example 11). The results suggest that when the concentration of the cocatalyst increases to a relative high level such as 16000 ppm, the problem of the rhodium catalyst precipitation at low water content can be entirely overcome.

TABLE 5

Effect of water content on rhodium catalyst concentration at different cocatalyst concentrations

| Example No. | Concentration of cocatalyst (ppm) | Concentration of rhodium catalyst (ppm) | | | | | | |
|---|---|---|---|---|---|---|---|---|
| | | 0 min | 10 min | 20 min | 30 min | 40 min | 50 min | 60 min |
| 7 | 4000 | 621 | 549 | 477 | 407 | 336 | 273 | 220 |
| 10 | 4000 | 608 | 581 | 521 | 495 | 485 | 408 | 362 |
| 9 | 16000 | 629 | 556 | 564 | 557 | 562 | 574 | 506 |
| 11 | 16000 | 644 | 614 | 594 | 583 | 571 | 549 | 503 |

* In examples 10 and 11, water content is 7 wt % and the concentration of methyl iodide is 20 wt %.

Examples 12~15

The cocatalyst according to the present invention is an excellent chelating agent, and may form a complex with transition metals other than rhodium. In other words, additional transition metals present in the reaction system will compete the cocatalyst of the present invention with the rhodium catalyst, and thus the performance for stabilizing rhodium catalyst by the cocatalyst of the present invention is adversely affected. On the other hand, metal iodide produced in the presence of the transition metals facilitates the dissolution of the rhodium catalyst.

In examples 12~15, the stabilizing effect of tri (carboxylmethyl)amine at different concentrations on the rhodium catalyst is studied, when 8,000 ppm of transition metals, for example iron, cobalt and nickel, are add to the reaction medium comprising 10 wt % of water, 14 wt % of methyl iodide and 5 wt % of free iodine.

During 60-minute reaction time, the concentration of the rhodium catalyst in the reaction medium changed with the reaction time is reported in Table 6. As shown in Table 6, higher concentration of cocalyst is required in the presence of transition metal elements, and the concentration of the rhodium catalyst increases as the concentration of the cocatalyst increases.

Table 6. Stabilizing effect of cocatalyst on rhodium catalyst in the presence of transition metal at a high concentration

TABLE 6

Stabilizing effect of cocatalyst on rhodium catalyst in the presence of transition metal at a high concentration

| Example No. | Concentration of cocatalyst (ppm) | Concentration of rhodium catalyst (ppm) | | | | | | |
|---|---|---|---|---|---|---|---|---|
| | | 0 min | 10 min | 20 min | 30 min | 40 min | 50 min | 60 min |
| 12 | 0 | 512 | 458 | 432 | 323 | 218 | 165 | 148 |
| 13 | 12000 | 546 | 532 | 516 | 526 | 444 | 369 | 336 |
| 14 | 24000 | 623 | 575 | 570 | 585 | 562 | 471 | 415 |
| 15 | 36000 | 663 | 600 | 568 | 617 | 596 | 601 | 536 |

* other reaction conditions: 10 wt % of water, 14 wt % of methyl iodide, about 4~5 wt % of free iodine, 5~8% of methyl acetate at 10 min and 3~5% after 20 min.

Examples 16~18

The carbonylation is carried out at the same conditions as those in examples 5~9, except that the cocatalyst used is replaced by 8,000 ppm of glutamic acid, aspartic acid and β-methyl-aspartic acid, respectively.

During 60-minute reaction time, the concentration of the rhodium catalyst in the reaction medium changed with the reaction time is reported in Table 7. As shown in Table 7, those amino acid cocatalysts have excellent stabilizing effects on the rhodium catalyst.

TABLE 7

Stabilizing effect of cocatalyst on the rhodium catalyst

| Example No. | Types of cocatalyst | Concentration of rhodium catalyst (ppm) | | | | | | |
|---|---|---|---|---|---|---|---|---|
| | | 0 min | 10 min | 20 min | 30 min | 40 min | 50 min | 60 min |
| 5 | — | 591 | 462 | 161 | 39 | 11 | 9 | 7 |
| 16 | Glutamic acid | 604 | 533 | 397 | 289 | 205 | 168 | 119 |
| 17 | Aspartic acid | 624 | 596 | 540 | 498 | 453 | 407 | 353 |

TABLE 7-continued

Stabilizing effect of cocatalyst on the rhodium catalyst

| Example No. | Types of cocatalyst | Concentration of rhodium catalyst (ppm) | | | | | | |
|---|---|---|---|---|---|---|---|---|
| | | 0 min | 10 min | 20 min | 30 min | 40 min | 50 min | 60 min |
| 18 | β-methyl-aspartic acid | 602 | 551 | 515 | 477 | 422 | 364 | 306 |

* other reaction conditions: 5 wt % of water, 20 wt % of methyl iodide, 4~5% methyl acetate at 10 min and 1~3% after 20 min.

What is claimed is:

1. A process for producing a carboxylic acid having (n+1) carbon atoms, comprising:
   carbonylating an alcohol having n carbon atoms, and/or an ester of said alcohol and said carboxylic acid with carbon monoxide in the presence of a catalytic system containing a rhodium catalyst, said process using a reaction medium for the carbonylation which comprises:
   (1) a rhodium catalyst;
   (2) an organic halide corresponding to said alcohol;
   (3) an ester of said alcohol and said carboxylic acid;
   (4) said carboxylic acid; optionally
   (5) water, a haloid acid, an inorganic halogen salt or an acetate; and
   (6) a cocatalyst selected from the group consisting of arginine, N-acetyl alanine, nitrogen- and oxygen-containing organic compounds represented by the following formula:

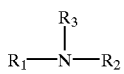

wherein $R_1$, $R_2$ and $R_3$ are identical or different, and each represents:

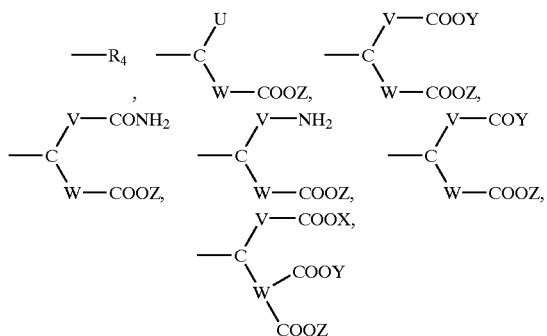

wherein
$R_4$ represents H, an aliphatic group having 1 to 6 carbon atoms, or an arylaliphatic or aromatic group having 6 to 10 carbon atoms;
U represents H, an aliphatic group having 1 to 6 carbon atoms or an arylaliphatic group or aromatic group having from 6 to 10 carbon atoms;
V and W each represents a covalent bond, an aliphatic group having from 1 to 6 carbon atoms or an arylaliphatic group or aromatic group having 6 to 10 atoms; and X, Y and Z each represents H, metal ion or an aliphatic group having 1 to 6 carbon atoms,
with the proviso that at least one of $R_1$, $R_2$ and $R_3$ is a group other than $R_4$.

2. The process according to claim 1, wherein said cocatalyst is selected from the group consisting of tri(carboxylmethyl)amine, di(carboxylmethyl)amine, methyl-di(carboxylmethyl)amine, 3-amino-1,1,3-propane-tricarboxylic acid and metal salts thereof.

3. The process according to claim 1, wherein said cocatalyst is selected from the group consisting of tyrosine, aspartic acid, β-methyl-aspartic acid, glutamic acid, glutamine, lysine and metal salts thereof.

4. The process according to claim 1, wherein the mole ratio of said cocatalyst to rhodium ranges from 0.5 to 200.

5. The process according to claim 4, wherein the mole ratio of said cocatalyst to rhodium ranges from 1 to 100.

6. The process according to claim 1, wherein the concentration of said rhodium catalyst in said reaction medium ranges from 200 to 5,000 ppm.

7. The process according to claim 6, wherein the concentration of said rhodium catalyst in said reaction medium ranges from 500 to 2,000 ppm.

8. The process according to claim 1, wherein said organic halide is alkyl iodide.

9. The process according to claim 1, wherein the concentration of said organic halide in said reaction medium ranges from 5 to 40 wt %.

10. The process according to claim 9, wherein the concentration of said organic halide in said reaction medium ranges from 10 to 30 wt %.

11. The process according to claim 1, wherein optionally 0 to 20 wt % of water is present in said reaction medium.

12. The process according to claim 11, wherein optionally 1 to 10 wt % of water is present in said reaction medium.

13. The process according to claim 1, wherein the concentration of said ester of said alcohol and said carboxylic acid in said reaction medium ranges from 0.1 to 30 wt %.

14. The process according to claim 13, wherein the concentration of said ester of said alcohol and said carboxylic acid in said reaction medium ranges from 0.1 to 5 wt %.

15. The process according to claim 1, wherein each of said inorganic halogen salt or said inorganic acetate is selected from halogen salt or acetate of alkali metal, alkaline-earth metal or transition metal.

16. The process according to claim 1, wherein each of said hydroiodic acid, said inorganic halogen salt or said acetate in said reaction medium has a concentration in the range of from 0 to 30 wt %.

17. The process according to claim 16, wherein each of said hydroiodic acid, said inorganic halogen salt or said acetate in said reaction medium has a concentration in the range of from 3 to 20 wt %.

18. The process according to claim 1, wherein said carbonylation is carried out under a condition where the concentration of said rhodium catalyst is greater than 500 ppm, the water content is less than 10 wt %, the concentration of said organic halide is greater than 10 wt % and the concentration of said ester is greater than 1.5 wt %.

19. The process according to any one of claims 1, 2, 3, or 4 to 18, wherein said alcohol is methanol and said organic halide corresponding to said alcohol is methyl iodide.

20. The process according to claim 19, wherein said reaction medium comprises 500 to 2,000 ppm of rhodium catalyst, 10 to 30 wt % of alkyl iodide, 0.1 to 5 wt % of methyl acetate, said cocatalyst having a mole ratio of 1 to 100 to said rhodium catalyst, 3 to 20 wt % of hydroiodic acid, said inorganic halogen salt or said acetate, and said acetic acid.

* * * * *